United States Patent
Esteve et al.

(10) Patent No.: US 6,566,404 B2
(45) Date of Patent: *May 20, 2003

(54) TREATMENT OF DRUG-INDUCED SLEEPINESS

(75) Inventors: Marc Esteve, Saint-Maur des Fosses (FR); Jacques Gertner, Paris (FR)

(73) Assignee: Institut Curie, Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/554,682

(22) PCT Filed: Nov. 19, 1998

(86) PCT No.: PCT/FR98/02478

§ 371 (c)(1),
(2), (4) Date: May 18, 2000

(87) PCT Pub. No.: WO99/25329

PCT Pub. Date: May 27, 1999

(65) Prior Publication Data

US 2003/0008925 A1 Jan. 9, 2003

(30) Foreign Application Priority Data

Nov. 19, 1997 (FR) .............................................. 97 14519

(51) Int. Cl.⁷ ............................................ A61K 31/165
(52) U.S. Cl. ....................................................... 514/618
(58) Field of Search .......................................... 514/618

(56) References Cited

FOREIGN PATENT DOCUMENTS

GB          1 584 462          2/1978

OTHER PUBLICATIONS

CA105:18327, Rambert, F. et al, J. Pharmacol., 1986, 17(1), 37–52, abstract.*
CA113:426, Delini–Stula, A, et al, Phychopharmacology, (Berlin), 1990, 101(1), 62–6, abstract.*
Roth, Thomas PhD et al., "Clinical Therapeutics, vol. 18, No. 4", *Etiologies and Sequelae of Excessive Daytime Sleepiness*, pp. 562–576, (1996).
Rambert, F.A., et al., "J. Pharmacol, (Paris), vol. 17, No. 1", *Profil Psychopharmacologique Original De L'Adrafinil Chez La Souris*, pp. 37–52, (1986).
"British National Formulary", "The Pharmaceutical Press, Chapter 4: *Central Nervous System*", pp. 156 and 166, (1986).

* cited by examiner

*Primary Examiner*—Rebecca Cook
(74) *Attorney, Agent, or Firm*—Foley & Lardner

(57) ABSTRACT

Benzhydrylsulphinyl derivatives are used to prevent the sleepiness associated with pain medication. Such derivatives selectively antagonize the hypnogenic effect of anti-pain treatment, such as morphine, without affecting the analgesic activity of the treatment and without creating other disadvantages. Methods of treatment and pharmaceutical compositions are provided.

10 Claims, No Drawings

TREATMENT OF DRUG-INDUCED SLEEPINESS

This is a 371 of PCT/FR98/02478 filed Nov. 19, 1998.

The invention relates to a new therapeutic use of benzhydrylsulphinyl derivatives.

More particularly, it relates to the use of such derivatives in situations of disorders in vigilance associated with an anti-pain treatment as applied in cases of serious diseases such as cancer, or for the painful after-effects of serious conditions.

About 40% of cancer patients have in fact to face pain in the course of the evolution of their disease.

This occurs either due to the unfavourable progression of the cancer, or due to the after-effects of the various treatments undertaken.

Several years ago the World Health Organization established a certain number of principles for dealing with pain in cancerology. In particular, it noted the important place which morphine should occupy in this treatment.

Thanks to this impetus and in spite of the cultural prejudices revolving around morphine, this product is now prescribed and accepted more and more readily.

Although its high efficacy on the analgesic level no longer has to be demonstrated, its side effects cannot be ignored, in particular the sleepiness which it causes. The various studies which have evaluated it report that it inconveniences 30 to 50% of patients under morphine where this is taken in the context of chronic treatment of cancer.

Current research approaches in the treatment of pain are mostly orientated towards the prospect of reducing these side effects, and in particular sleepiness.

The products available to the clinician to date are essentially amphetamine derivatives. However, such derivatives are the source of major disadvantages associated with their undesirable cardiovascular and neuropsychic effects on the one hand, and dependence during long-term use on the other hand.

In investigating a solution to this problem, the inventors orientated themselves towards evaluation of the effects, in the context of morphine treatment, of compounds known for their awakening power and their ability to stimulate vigilance.

They were thus able to demonstrate unexpectedly that such compounds selectively antagonized the hypnogenic effect of morphine without affecting its analgesic activity and without creating other disadvantages.

It has also been demonstrated that these selective antagonist effects were also exerted on the sleepiness states induced by medicaments conventionally administered with morphine, such as analgesics, antidepressants and anxiolytics.

The invention thus provides the use for the manufacture of medicaments of compounds which are capable of exerting an awakening effect in situations of disorders in vigilance associated with a morphine treatment (this expression encompassing the use of morphine or derivatives thereof with, where appropriate, the medicaments usually used in this type of context).

It also provides new pharmaceutical presentations which allow all the required effects to be obtained conjointly.

According to the invention, benzhydrylsulphinyl compounds corresponding to the general formula (I)

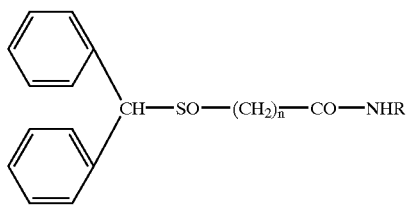

in which
each of the rings can be substituted by one or more F, Cl, Br, $CF_3$, $NO_2$, $NH_2$, $C_1$–$C_4$-alkyl, $C_1$–$C_4$-alkoxy or methylenedioxy groups;
R represents a hydroxyl group, a hydrogen atom, a $C_1$–$C_4$-alkyl group, a $C_1$–$C_4$-hydroxyalkyl group or a $R_1R_2N$—Y— group, where Y is a linear or branched $C_1$–$C_4$-hydrocarbon radical, and $R_1$ and $R_2$ are identical or different and each represent a hydrogen or a $C_1$ to $C_4$-alkyl or $NR_1R_2$ represents a 5- or 6-membered heterocyclic radical containing, where appropriate, a second heteroatom such as N or O, and which can be substituted;
n is an integer equal to 1, 2 or 3; and their addition salts when R contains a basic radical,
are used for the manufacture of the said medicaments.

Preferably, R represents an —OH group or a hydrogen atom.

The invention particularly provides the use of benzhydrylsulphinyl-acetohydroxamic acid of the formula (II)

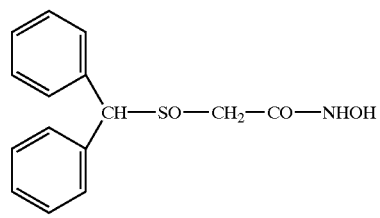

called adrafinil by its international nonproprietary name and marketed under the brand name Olmifon®.

It more particularly provides the use of its metabolite, that is to say benzhydrylsulphinyl-acetamide of the formula (III)

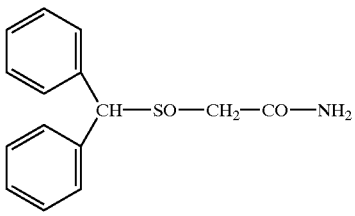

corresponding to the international nonproprietary name modafinil and marketed under the brand name Modiodal®.

The compounds used according to the invention are known for their selective stimulating activity on awakening and vigilance and are widely used for treatment of narcolepsy and idiopathic hypersomnia.

Surprisingly, when used in the context of morphine treatment, combined, where appropriate, with administration of antidepressants and/or anxiolytics and/or analgesics, they allow a considerable reduction in the state of sleepiness evaluated by the Epworth scale, while ensuring the analgesic properties of morphine and the properties of antidepressant, anxiolytic or analgesic medicaments are maintained. The patient is thus re-established in a satisfactory relational life.

According to an advantageous embodiment of the invention, the said medicaments comprise at least one compound of the formula (I) in an amount of 50 to 600 mg, preferably 100 to 300 mg.

During preparation of the medicaments, the active principles are mixed with pharmaceutically acceptable vehicles for the chosen mode of administration.

For administration by the oral route, the medicaments are thus prepared in the form of gelatine capsules, tablets, coated tablets, capsules and analogous products.

For administration by the injectable route, the medicaments are in the form of solutions in injectable ampoules.

Administration by the transcutaneous route, in the form of a patch, can also be used.

As shown in the examples, very favourable results were obtained clinically with administrations of about 200 to 400 mg Modiodal® per day, in 1 or 2 doses, and about 1,200 to 1,800 mg Olmifon® per day, in 2 doses.

According to another aspect utilizing the effects resulting from conjoint administration of analgesics and/or antidepressants and/or anxiolytics on the one hand and products which stimulate vigilance on the other hand, the invention provides a pharmaceutical presentation, characterized in that it comprises the two types of medicaments respectively, with a suitable information leaflet.

In this presentation, the medicaments are in galenical forms suitable for the chosen administration route.

In order to illustrate the invention, but without limiting its scope, the results of observations made confidentially on patients in the context of hospitalization are reported below. The consent of the patients was obtained after the compassionate grounds of the prescription had been explained to them.

CASE NO. 1

Madame M., born in 1937, has been suffering from cancer of the right breast since 1991. After having undergone local surgical and radiotherapy treatment, in 1993 she has the first pain revealing osseous metastatic diffusion.

Chemotherapy treatment is initiated immediately.

These first painful difficulties lead her to seek advice regarding the pain, where morphine treatment is rapidly initiated. This alleviates it, but causes a significant degree of sleepiness until its prescription is limited, and indeed stopped, at the request of the patient. Between 1994 and 1997, Madame M. regularly sought advice regarding the pain.

The morphine treatment is resumed on several occasions because of the occurrence of painful episodes relating to the outbreak of new osseous metastatic foci,
and then stopped when the efficacy of the radiotherapy treatment then instituted is achieved.

From January 1996, the morphine treatment could no longer be interrupted. Its efficacy is moderated because of the limitation in the progression of its dosages having regard to the sleepiness which it causes.

Given the progression of painful phenomena, at the end of October 1997 the patient is hospitalized. At this point in time the dosage of Mosocontin® is 100 mg twice every 24 hours, her EVA score is 60, and her sleepiness evaluated on the Epworth scale is 20. The Moscontin® is increased to 160 mg twice every 24 hours. After stabilization of the analgesic level at an EVA score of 30, treatment with Modiodal®, initially in a dosage of 100 mg and then rapidly 200 mg, is initiated. This dosage allows her Epworth score to drop below 10. This quality of awakening has enabled her to resume family relationships of a better quality. The efficacy of the analgesia and her better vigilance level has enabled her to take accompanied walks. A nutritional recovery manifesting itself by a weight increase of 2 kg in 10 days is also to be noted in this patient.

CASE NO. 2

Madame B., born in 1952, has had breast cancer since 1987.

Its course has developed to the metastatic mode at the pulmonary, hepatic and osseous levels.

In September 1997, very disabling right costal pain occurs, which leads her to seek advice regarding the pain. Together with flash radiotherapy treatments, analgesic treatment is started, which combines dextropropoxyphene, paracetamol and clonazepam. The patient has already taken oral morphine in the course of her disease, and dreads this product because of its hypnotic effects. She wants to continue to pursue her profession. Given the persistence of painful phenomena, transition to oral morphine proves obligatory. The treatment is performed with Skenan® in a dose of 30 mg twice every 24 hours. At the end of 48 hours the patient is seen again. She evaluates her pain at 30 on the EVA scale, but feels very sleepy. She does not want to increase the morphine dosage. Seven days later the patient seeks advice again, the pain is rated at 60 and her state of sleepiness is significant, rated at 16 on the Epworth scale. Hospitalization with the aim of balancing pain and sleepiness is agreed.

The doses of Skenan® are doubled directly and are immediately combined with 200 mg Modiodal®. The result is rapidly favourable both at the analgesic level (EVA 20) and at the vigilance level (rating of less than 10). On discharge from hospital, Madame B. could resume her professional activities.

CASE NO. 3

Monsieur L., born in 1922, has been treated since 1994 for prostate cancer. In July 1997 a cervical vertebral localization manifests itself by symptoms of medullary compression. A laminectomy is performed in the first instance, followed by radiotherapy. These treatments allow the neurological lesions to be stabilized. However, Monsieur L. still has cervical pain which leads to the start of analgesic treatment with sustained release oral morphine. This treatment, consisting of administration of Moscontin® in an amount of 30 g twice every 24 hours will be poorly tolerated both at the digestive level (nausea) and at the cognitive level (significant disorientation). An initial hospitalization is proposed. It will allow continuous treatment with subcutaneous morphine from an electrical syringe combined with clonazepam by the oral route to be started. The patient leaves hospital and his pain rating on the EVA scale is 30. However, a significant sleepiness persists.

At the vertebral level, the symptoms of neurological compression reappear progressively. Since care conditions are becoming difficult at home, Monsieur L. is rehospitalized in mid-October. At the start of hospitalization his cervical pain is still controlled by a moderate dose of morphine (40 mg) by the subcutaneous route. However, he has a major state of sleepiness preventing any dialogue being conducted with his family. (20 on the Epworth scale). Treatment with Modiodal® 100 mg and then 200 mg allows him to recover a clearly superior state of vigilance rated at 12.

CASE NO. 4

Madame Q., born in 1929, underwent enucleation of the left eye in 1995 for a choroid melanoma beyond any conservative treatment means. In 1997 hepatic metastases appear, for which a chemotherapy treatment is performed. In the month of October 1997 she seeks advice for the vertebral pain rated 60 on the EVA. A morphine treatment by the oral route with Moscontin®, 100 mg×2, allows these painful phenomena to be stabilized (EVA=40), but at the expense of a disabling state of sleepiness. Hospitalization with the aim of regulating the problem of sleepiness is agreed by the patient. Treatment with modafinil in a dose of 300 mg, achieved progressively, allows the sleepiness index to change from 23 to 11.

CASE NO. 5

Madame B., born in 1911, is under supervision for breast cancer. Its metastatic evolution has developed to the osseous level. She has a very painful supracotyloid metastasis preventing any movement of the hip. Radiotherapy was not able to regulate the pain problem. A morphine treatment is instituted at home, and very rapidly causes severe sleepiness rendering care at home impossible. Analgesia is not correctly obtained (EVA=40). Hospitalization allows regulation of the analgesic problem using morphine by the subcutaneous route in an amount of 40 mg (equivalent dose greater than the dose which she was taking by the oral route) and of the sleepiness by a dose of 200 mg modafinil per day (the sleepiness index changes from 22 to 15).

These pilot cases demonstrate the efficacy of modafinil on morphine sleepiness, and indeed on that associated with clonazepam.

The invention thus provides means for activating the awakening structures of a patient under morphine treatment causing a state of sleepiness without having an effect on the peripheral system. The invention in particular allows a return at least partially, and indeed totally, to a normal physical condition for the patient suffering from cancer or D suffering from painful after-effects of serious conditions. It also allows morphine tolerance to be increased.

What is claimed is:

1. A method of antagonizing the hypnogenic effect of morphine treatment comprising administering to a patient undergoing said treatment a compound of the formula

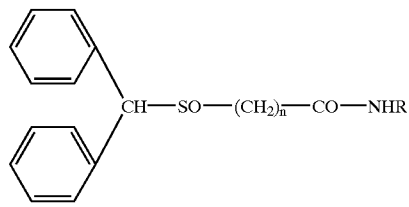

wherein each of the rings is optionally substituted by one or more substituents selected from the group consisting of F, Cl, Br, $CF_3$, $NO_2$, $NH_2$, $C_1$–$C_4$-alkyl, $C_1$–$C_4$-alkoxy and methylenedioxy;

R is a hydroxyl group, a hydrogen atom, a $C_1$–$C_4$-alkyl group or a $C_1$–$C_4$-hydroxyalkyl group;

n is an integer equal to 1, 2, or 3; or an addition salt thereof when R is a basic radical.

2. The method of claim 1, wherein R is a hydroxyl group or a hydrogen atom.

3. The method of claim 2, wherein said compound has the formula

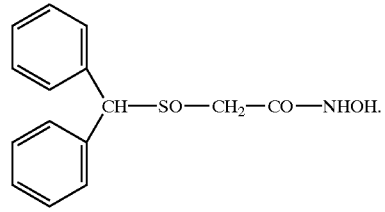

4. The method of claim 2, wherein said compound has the formula

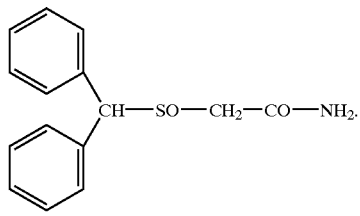

5. The method of claim 1, wherein said patient is administered 50 to 600 mg of said compound.

6. The method of claim 1, wherein said patient is administered 100 to 300 mg of said compound.

7. The method of claim 1, wherein said compound is administered to said patient orally in the form of gelatin capsules, tablets, coated tablets or capsules.

8. The method of claim 1, wherein said compound is injected into said patient.

9. The method of claim 1, wherein said compound is administered to said patient transcutaneously using a patch.

10. A pharmaceutical composition comprising morphine, a compound of the formula

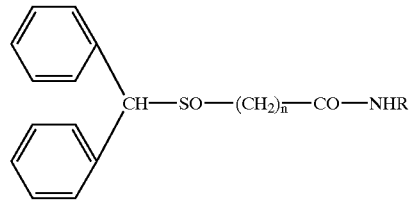

wherein each of the rings is optionally substituted by one or more substituents selected from the group consisting of F, Cl, Br, $CF_3$, $NO_2$, $NH_2$, $C_1$–$C_4$-alkyl, $C_1$–$C_4$-alkoxy and methylenedioxy;

R is a hydroxyl group, a hydrogen atom, a $C_1$–$C_4$-alkyl group or a $C_1$–$C_4$-hydroxyalkyl group;

n is an integer equal to 1, 2, or 3; or an addition salt thereof when R is a basic radical, and a pharmaceutically acceptable vehicle.

* * * * *